United States Patent
Malin

(10) Patent No.: US 7,832,921 B2
(45) Date of Patent: Nov. 16, 2010

(54) STORAGE DEVICE FOR LABORATORY SAMPLES HAVING STORAGE RACKS AND A SHAKER

(75) Inventor: Cosmas Malin, Mauren (LI)

(73) Assignee: Liconic AG, Mauren (LI)

( * ) Notice: Subject to any disclaimer, the term of this patent is extended or adjusted under 35 U.S.C. 154(b) by 1165 days.

(21) Appl. No.: 11/429,438

(22) Filed: May 8, 2006

(65) Prior Publication Data

US 2006/0289371 A1   Dec. 28, 2006

(30) Foreign Application Priority Data

May 9, 2005   (CH) ..................... 0813/05

(51) Int. Cl.
*B01F 11/00* (2006.01)

(52) U.S. Cl. ..................... 366/208

(58) Field of Classification Search ......... 366/108–117, 366/124, 208–219

See application file for complete search history.

(56) References Cited

U.S. PATENT DOCUMENTS

| | | | | |
|---|---|---|---|---|
| 3,430,926 A | * | 3/1969 | Liobis et al. ................ | 366/212 |
| 3,830,474 A | * | 8/1974 | Tannenbaum ............... | 366/203 |
| 4,118,801 A | * | 10/1978 | Kraft et al. ................. | 366/111 |
| 4,202,634 A | * | 5/1980 | Kraft et al. ................. | 366/111 |
| 4,305,668 A | * | 12/1981 | Bilbrey ...................... | 366/111 |
| 4,643,879 A | | 2/1987 | Hanaway | |
| 4,747,693 A | * | 5/1988 | Kahl .......................... | 366/208 |
| 4,750,845 A | * | 6/1988 | Nabetani ................... | 366/208 |
| 4,834,548 A | * | 5/1989 | Tempel et al. .............. | 366/208 |
| 5,346,303 A | * | 9/1994 | Heinonen et al. ........... | 366/208 |
| 5,372,425 A | * | 12/1994 | Tannenbaum et al. ....... | 366/208 |
| 5,558,437 A | * | 9/1996 | Rode .......................... | 366/208 |
| 5,577,837 A | * | 11/1996 | Martin et al. ............... | 366/145 |
| 5,593,228 A | * | 1/1997 | Tannenbaum ............... | 366/209 |
| 5,645,500 A | | 7/1997 | Borden | |
| 5,735,587 A | | 4/1998 | Malin et al. | |
| 6,129,428 A | | 10/2000 | Helwig et al. | |
| 6,190,032 B1 | * | 2/2001 | Choda ........................ | 366/208 |
| 6,475,776 B1 | | 11/2002 | Higuchi | |
| 6,478,524 B1 | | 11/2002 | Malin | |
| 6,536,859 B1 | | 3/2003 | Bathe | |
| 6,568,770 B2 | | 5/2003 | Gonska et al. | |
| 7,338,199 B2 | * | 3/2008 | Hafner ....................... | 366/208 |
| 2004/0004415 A1 | | 1/2004 | Melching | |
| 2004/0115101 A1 | | 6/2004 | Malin | |
| 2004/0170082 A1 | | 9/2004 | Heeg et al. | |

FOREIGN PATENT DOCUMENTS

| | | |
|---|---|---|
| DE | 100 09 555 A1 | 3/2001 |
| DE | 103 02 809 A1 | 8/2004 |

(Continued)

*Primary Examiner*—Charles E Cooley
(74) *Attorney, Agent, or Firm*—Browdy and Neimark, PLLC

(57) ABSTRACT

The invention provides a storage device with storage racks and a shaker where the undesired horizontal oscillations of the upper ends of the storage racks are small. For this purpose, rotating bodies with non-horizontal end faces are provided, each of which is contacted by a follower member, with the follower member carrying out an up and down movement when the respective rotating body rotates. In a second embodiment, a moving counterweight assembly is provided that counteracts the oscillations. The counterweight assembly is connected to the upper end section of the storage racks and includes a vertically displaceable counterweight. The counterweight is mounted eccentrically on rotating tables.

19 Claims, 7 Drawing Sheets

FOREIGN PATENT DOCUMENTS

| | | |
|---|---|---|
| EP | 0 569 214 A | 11/1993 |
| EP | 0 569 214 A2 | 11/1993 |
| EP | 1 354 623 A1 | 10/2003 |
| EP | 1 443 101 A | 8/2004 |
| GB | 2 386 153 A | 9/2003 |
| GB | 2451491 A * | 2/2009 |

* cited by examiner

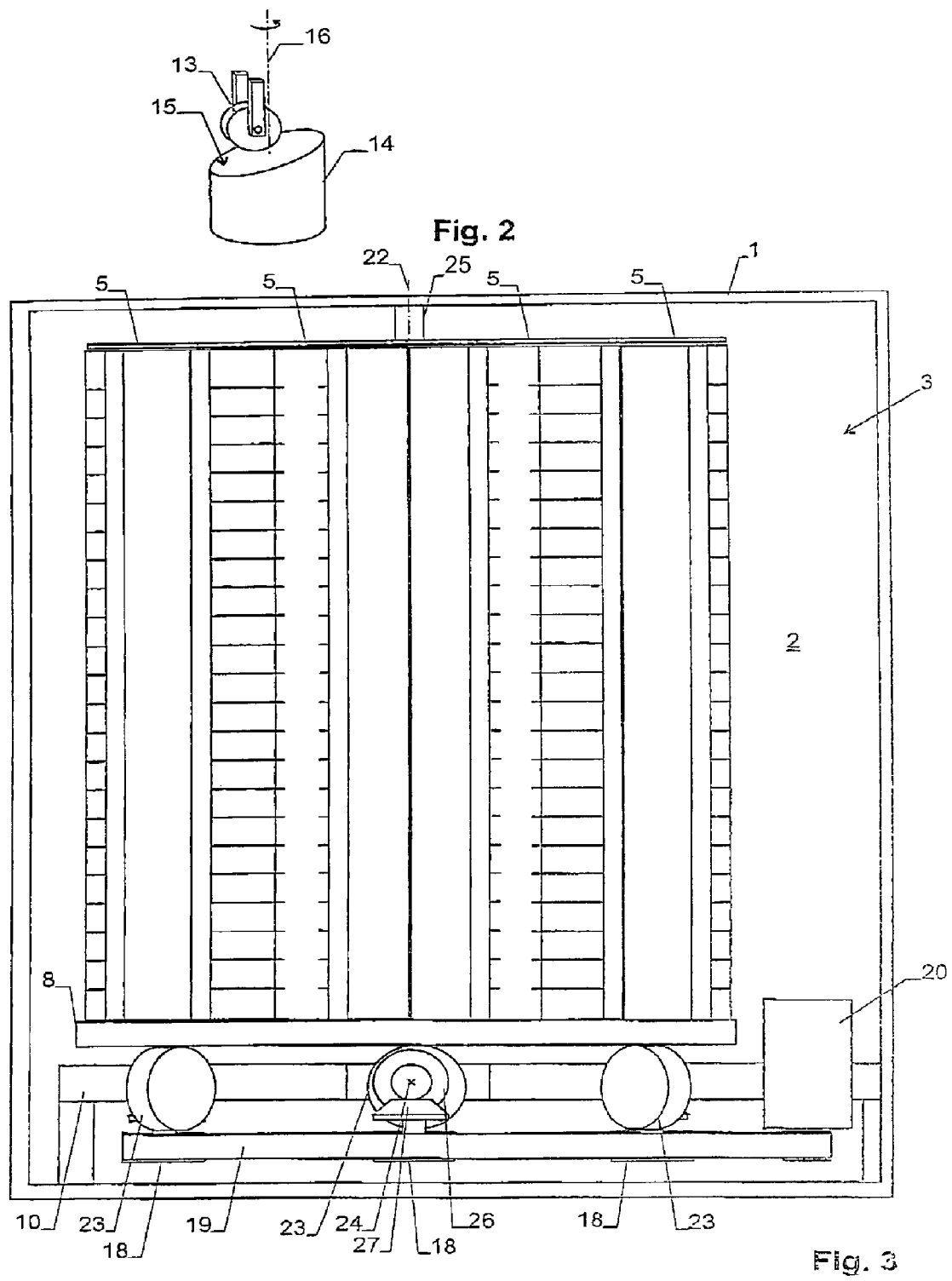

STORAGE DEVICE FOR LABORATORY SAMPLES HAVING STORAGE RACKS AND A SHAKER

CROSS REFERENCE TO RELATED APPLICATIONS

This application claims the priority of Swiss patent application 00813/05, filed May 9, 2005, the disclosure of which is incorporated herein by reference in its entirety.

BACKGROUND OF THE INVENTION

The invention relates to a storage device for laboratory samples comprising at least one storage rack and a shaker drive. The invention also relates to climate controlled cabinets having such a storage device.

In automated essays, e.g. in microbiology, samples are stored in so-called micro titer plates having a large number of small wells. Because of the large number of probes to be investigated, a large number of plates are used in a test run. Typically, the plates are stored in tower-shaped storage racks. Each storage rack is adapted to receive a plurality of micro titer plates (or similar laboratory samples) on top of each other. For certain applications, it is necessary to shake the samples during certain time periods.

EP 1 443 101 describes a storage device in a climate controlled cabinet that comprises a shaker drive, which shakes a storage rack carrier. A number of storage racks, e.g. two, are mounted to the rack carrier. Since the storage racks are comparatively high, undesired oscillatory movements of the upper ends of the storage racks can occur during shaking. This limits the shaking frequency and amplitude, makes it necessary to use a very sturdy setup, and leads to undesired noise and vibrations as well as to a shaking amplitude that is different for different storage locations.

BRIEF SUMMARY OF THE INVENTION

Hence, it is a general object of the invention to provide a storage device or a climate controlled cabinet that allows an efficient shaking of even high storage racks.

Now, in order to implement these and still further objects of the invention, which will become more readily apparent as the description proceeds, the storage rack, in a first aspect of the invention, is manifested by the features that it comprises
 a shaker drive,
 a rack carrier being driven by said shaker drive for performing a shaking motion with horizontal component,
 at least one storage rack arranged on the rack carrier, which storage rack comprises storage locations for a plurality of laboratory samples on top of each other, and
 a counterweight assembly connected to an upper end section of the storage rack and being driven to exert a force opposite to the shaking motion in order to counteract an oscillation of the upper end section of the storage rack.

Hence, the counterweight assembly is connected to the storage rack(s) at an upper end section thereof and is driven such that it exerts an oscillatory force opposite to the shaking motion to counteract the undesired oscillations. In this manner, undesired excessive motion of the upper end of the storage rack(s) is reduced.

In an advantageous embodiment the counterweight assembly comprises a moving part that is driven opposite to the shaking motion of the storage racks and can thus generate the desired force.

In a second aspect of the invention, the storage device comprises
 a shaker drive,
 a rack carrier driven by said shaker drive for performing a shaking motion, and
 at least one storage rack arranged on the rack carrier, said storage rack comprising a plurality of storage locations for laboratory samples on top of each other,
 wherein said shaker drive is adapted to shake the storage carrier in a vertical direction.

Hence, the object is achieved by a vertical shaking motion. This prevents a lateral oscillation of the storage rack and leads to highly homogeneous acceleration forces within the whole storage rack. A further advantage of this arrangement is the fact that an improved mixing within the small fluid volumes is achieved because of the vertical shaking motion.

Advantageously, the rack carrier can be moved upwards and downwards by the shaker drive without being tilted such that the acceleration forces act in vertical direction only.

In an advantageous embodiment the shaker drive comprises a rotating body driven for rotation. The rotating body has a non-horizontal end face. At least one follower member abuts against the end face and performs an up and down motion (in respect to the rotating body) while the rotating body rotates. In this matter a rotational motion can be efficiently transformed into a vertical up and down movement.

In order to achieve a homogenous vertical shaking motion, several rotating bodies and follower members can be provided, wherein the rotating bodies are driven for rotation by a common belt.

The invention also relates to a climate controlled cabinet with such a storage device, where the storage racks can be stored under controlled temperature and, where necessary, under controlled gas composition, in particular under controlled humidity.

In all aspects of the invention large acceleration forces can be achieved such that even small amounts of fluid can be mixed efficiently.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 2 is a detail of the shaker drive of FIG. 1, FIG. 3 is a second embodiment of a climate controlled cabinet with a shaker drive for vertical shaking.

DETAILED DESCRIPTION OF THE INVENTION

Figure 1:
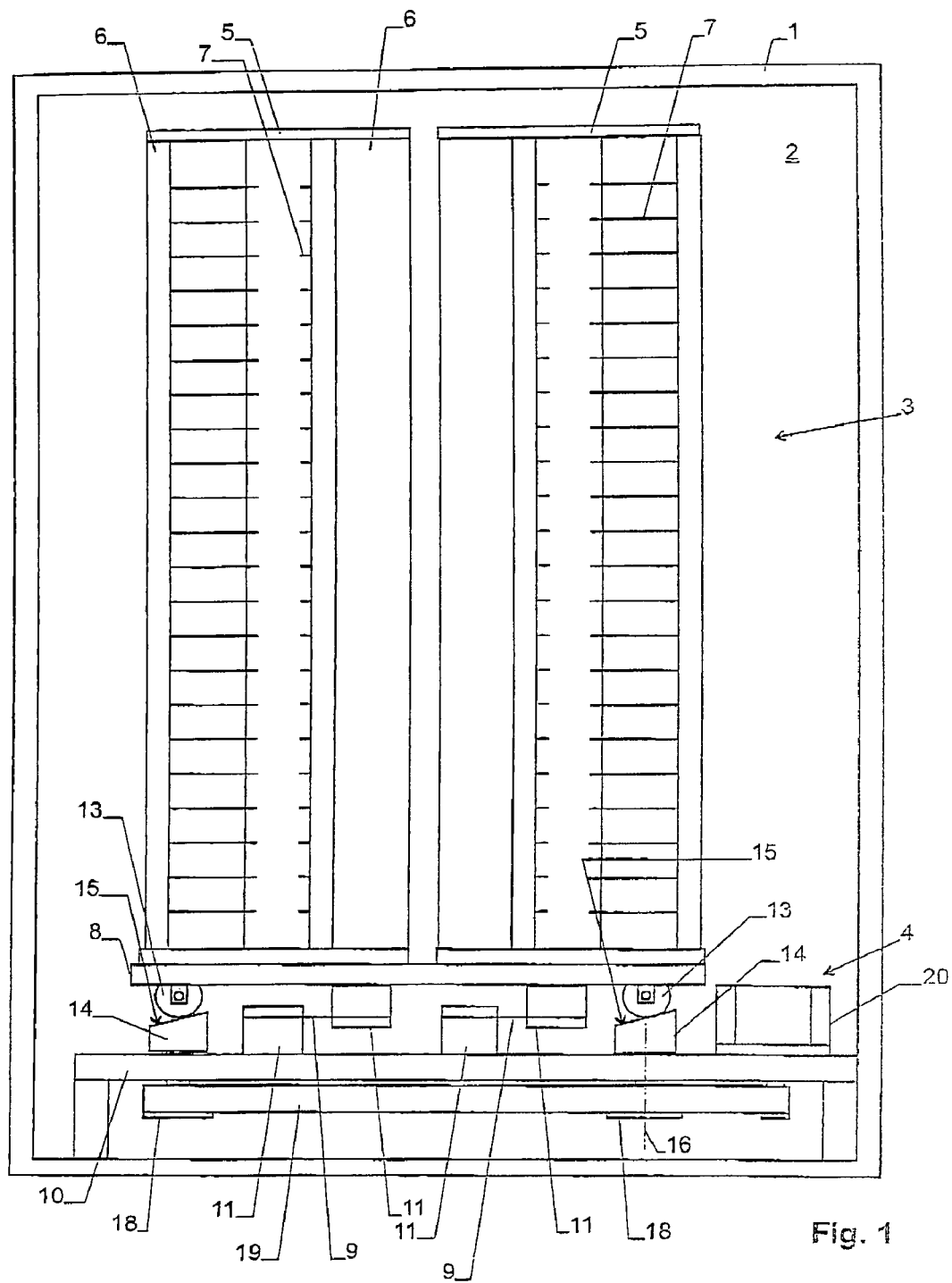
FIG. 1 is a climate controlled cabinet with a shaker drive for vertical shaking.

The climate controlled cabinet of FIG. 1 comprises an interior space 2 holding a storage device 3 with shaker drive 4. The climate controlled cabinet comprises means to generate a controlled climate in its interior space 2. It can be equipped for manual and/or automatic access. The climate controlled cabinet of FIG. 1 e.g. corresponds to the device shown in U.S. Pat. No. 6,478,524 and has two storage racks 5 arranged in a "V"-shaped configuration. The shaker drive of FIG. 1 is, however, also suited for storage devices with only one or substantially more storage racks. It can also be used for storage devices that are not arranged in a climate controlled cabinet. The same is true for the shaker drives 4 and storage devices 3 described further below.

Each storage rack 5 comprises two vertical side walls 6, each having a plurality of ledges 7. The ledges 7 form a corresponding number of storage locations arranged above each other for receiving the laboratory samples. In a particularly important application, the laboratory samples are micro titer plates. These have a plurality of small wells for receiving fluids. Micro titer plates have, as a rule, a standard size with a footprint of 127.76 mm×85.48 mm (each +/−0.5 mm) according to standard ANSI/SBS 1-2004, Jan. 8, 2004, "for microplates—footprint dimensions". The storage locations are adapted to these dimensions.

The storage racks 5 are mounted to a common rack carrier 8 and are affixed thereto in suitable, releasable manner. For this purpose, rack carrier 8 provides an horizontal mounting surface with holder rails as described below.

Rack carrier 8 can be moved vertically and is fixedly held in horizontal direction. In the embodiment of FIG. 1, this is achieved by means of two plate springs 9 arranged between rack carrier 8 and a stationary base body 10. The plate springs are arranged horizontally such that they allow a vertical motion of the rack carrier 8 but prevent it from moving horizontally. For this purpose, mounting blocks 11 are arranged to both, base body 10 and rack carrier 8, each pair of mounting blocks 11 holding one plate spring in horizontal orientation.

To generate the shaking motion, four bearings having rotating bodies with inclined end faces are provided. Four follower members 13 are mounted to the rack carrier, each of which rests against a non-horizontal end-face 15 of a rotating body 14 of the shaker drive.

As described in the following and as can in particular be seen in FIG. 2, each rotating body 14 is driven for rotation about a vertical rotation axis 16. Each end face 15 is flat and inclined in respect to rotation axis 16 of its respective rotating body 14, the respective follower member 13 touches the end face 15 at a distance from the rotation axis.

If rotating body 14 is rotated about rotation axis, 16, the respective follower member 13 carries out an up and down movement in respect to rotating body 14. The plate springs ensure that the follower members 13 do not lift off the end surfaces 15 even at high shaking frequencies.

As shown in FIG. 1, the rotating bodies 14 are mounted to base body 10. Each rotating body 14 is connected to a driving gear 18. A gear belt 19 is led around all driving gears 18 and driven by a motor 20. This ensures that the rotating bodies are driven in synchronicity such that the follower members 13 move synchronously.

As can in particular be seen in FIG. 2, each follower member 13 of the present invention is a roller running on end face 15 and touching the same at only a distance from rotating axis 16. By using rollers, frictional losses can be small. It is, however, also possible to use low friction gliders as follower members instead of rollers.

Instead of a flat, inclined end surface 15, a corrugated or bent end surface 15 can be used. It is also possible to mount the follower members 13 to base plate 10 and the rotating bodies 14 (with the shaker motor 20) to rack carrier 8.

Instead of the shaker drive shown in FIGS. 1 and 2, another type of shaker drive can be used by means of which rack carrier 8 can be moved up and down. Advantageously, a purely vertical movement is generated in order to fully avoid the problematic, lateral displacement of the storage racks 5.

For example, a direct, purely electromagnetic vibrational drive can be used.

Another variant of a shaker drive is shown in FIG. 3.

This figure again shows a storage device 3 in a climate controlled cabinet 1. In this embodiment, however, storage device 3 comprises more than two storage racks 5, which are arranged rotatably about a vertical axis on a carousel. Such an assembly is e.g. described in WO 02/059251. The carousel in FIG. 3 is formed by rack carrier 8.

In this embodiment the shaker drive 4 is designed not only to shake rack carrier 6 vertically, but also to rotate it about its vertical central axis 22, i.e. both movements are generated by the same motor 20.

Also in this embodiment, the storage racks rest on rack carrier 8, which can be moved vertically but not horizontally. In addition to this, rack carrier 8 can be rotated about its vertical central axis. For this purpose, it is held in a rotational bearing 25, which can e.g. comprise a cylindrical bushing located at central axis 22.

Rack carrier 8 rests on three rollers 23, which are arranged symmetrically about central axis 22 of the carousel. Each roller is held eccentrically on a horizontal shaft 24, wherein the horizontal shaft extend radially in respect to central axis 22. Each shaft 24 is mounted to stationary base body 10 and holds a first, concentric bevel gear 26, which forms an angled gearing together with a second bevel gear 27. The second bevel gears 27 are synchronously driven by means of a common gear belt 19 and a motor 20.

When gear belt 19 is set in motion, rollers 23 start to rotate eccentrically about the roller shafts 24 and convey a substantially constant rotational movement and, at the same time, an alternating vertical up and down movement to rack carrier 8 such that the storage racks 5 are shaken.

In a variant of this embodiments, only one of the rollers 23 is driven.

By means of the embodiment of FIG. 3, it becomes possible to rotate and shake the carousel of the storage racks 5 with a single motor only.

It is, however, also possible to combine a different type of shaker drive, such as a shaker drive with bearings as shown in FIG. 1, with a carousel drive. In this case, the device has a rotational drive for rotating the storage racks about vertical axis 22 and a shaker drive for generating an up and down motion of the storage racks. This is, constructively, somewhat more complicated, but it allows to choose the shaking frequency independently from the rotational speed.

In order to obtain sufficient mixing with standard micro titer wells, the shaking motion of the embodiments shown so far should have an amplitude between 0.1 and 10 mm.

As mentioned initially, the present invention also relates to a storage device where the storage racks are shaken horizontally. A corresponding embodiment is shown in FIGS. 4 to 7.

Figure 4:
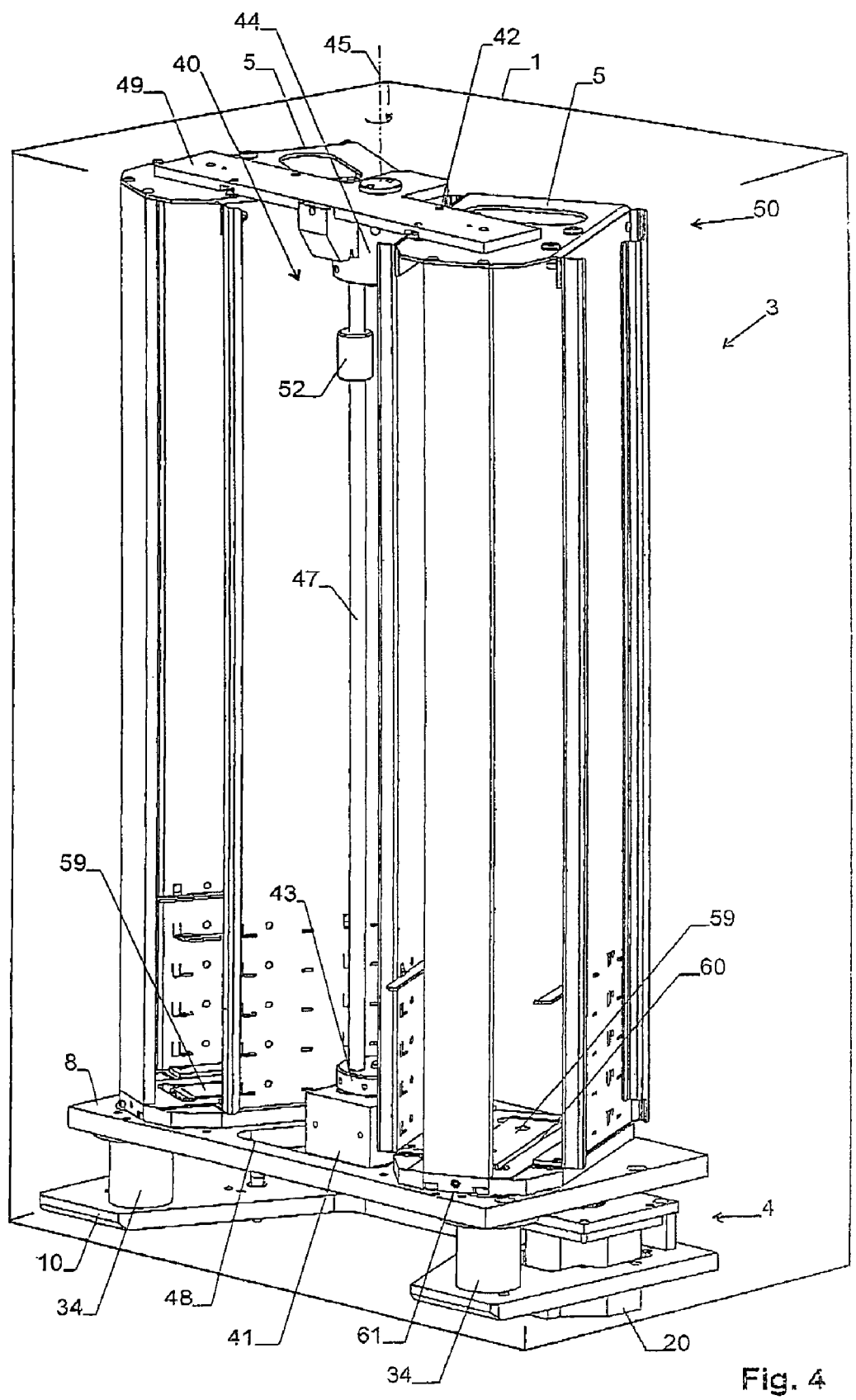
FIG. 4 is a third embodiment of the invention.
Figure 5:
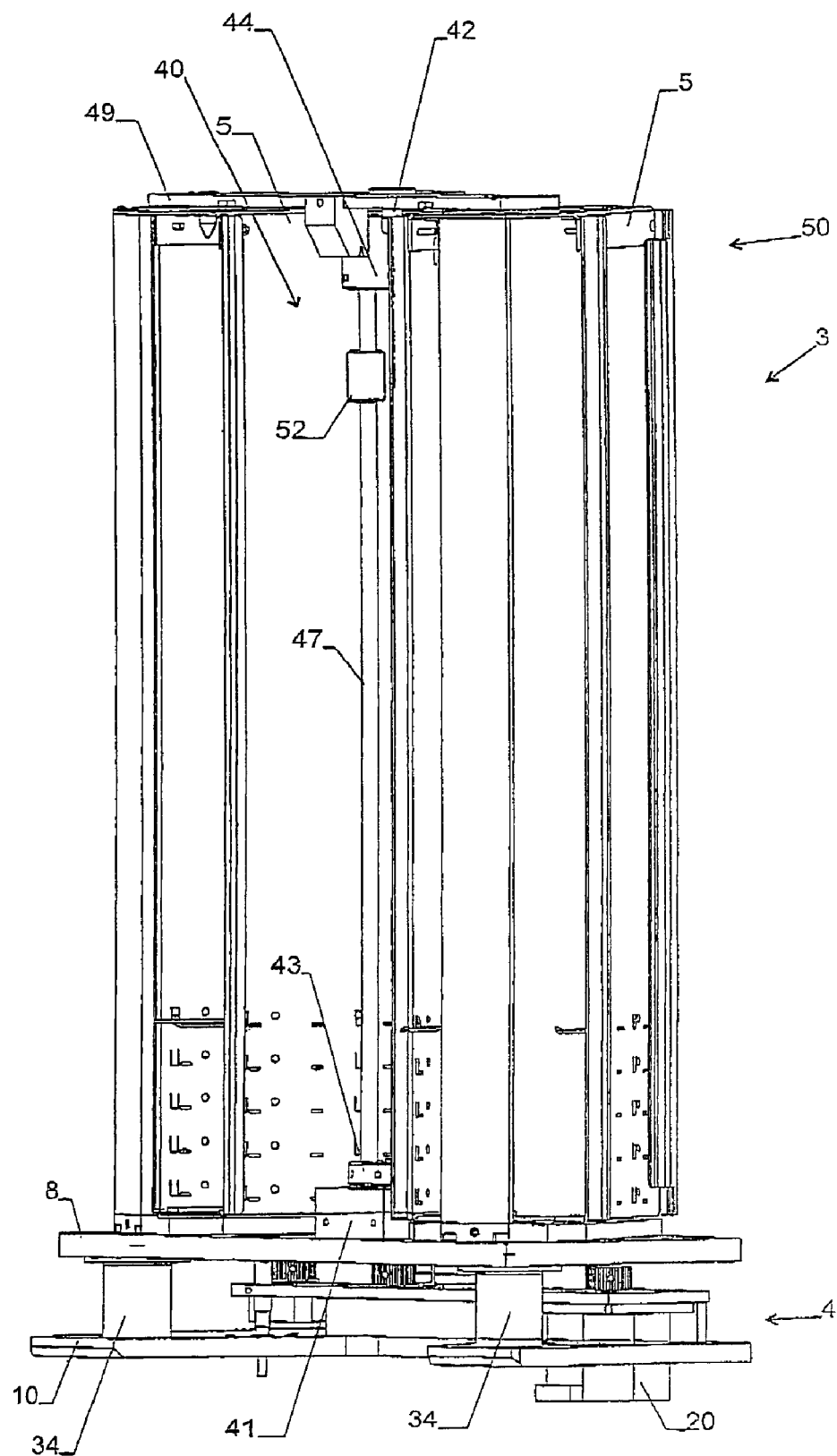
FIG. 5 is the embodiment of FIG. 4 seen from a somewhat different angle.

This is also a storage device 3 with two storage racks 5 arranged with "V"-shaped footprint, which can e.g. be located in a climate controlled cabinet 1 (as indicated in FIG. 4). However, this storage device can also be used without a climate controlled cabinet. In addition, the number of the storage racks 5 can be adapted to the respective needs, and the concept can also be used in carousel shaped geometries of the storage racks, but also for a single storage rack only.

The two storage racks 5 are, as in FIG. 1, arranged on a rack carrier 8, which is set into motion by a shaker drive 4.

In contrast to the embodiment of FIG. 1, the shaker drive of FIGS. 4-7 generates a horizontal shaking motion, or at least a shaking motion having a horizontal component of movement. For this purpose, a motor 20 drives, directly or via a gear belt 19 shown in dashed lines in FIGS. 6 and 7, three gears 30, 31, 32. Motor 20 and gears 30, 31, 32 are arranged on stationary base body 10.

Pins 33 extending upwards are eccentrically mounted to the two outer gears 30, 31 and engage corresponding openings of rack carrier 8 to convey their eccentric motion thereto. When gears 30, 31 rotate, an eccentric horizontal shaking motion of rack carrier 8 is generated.

Rack carrier 8 is held by the pins 33 as well as two frictional bearings 34, namely in such a manner that it can move horizontally but cannot tilt. An additional vertical shaking motion is not achieved with the embodiment of FIGS. 5-7, but could be generated by other shaker drives.

Figure 7:
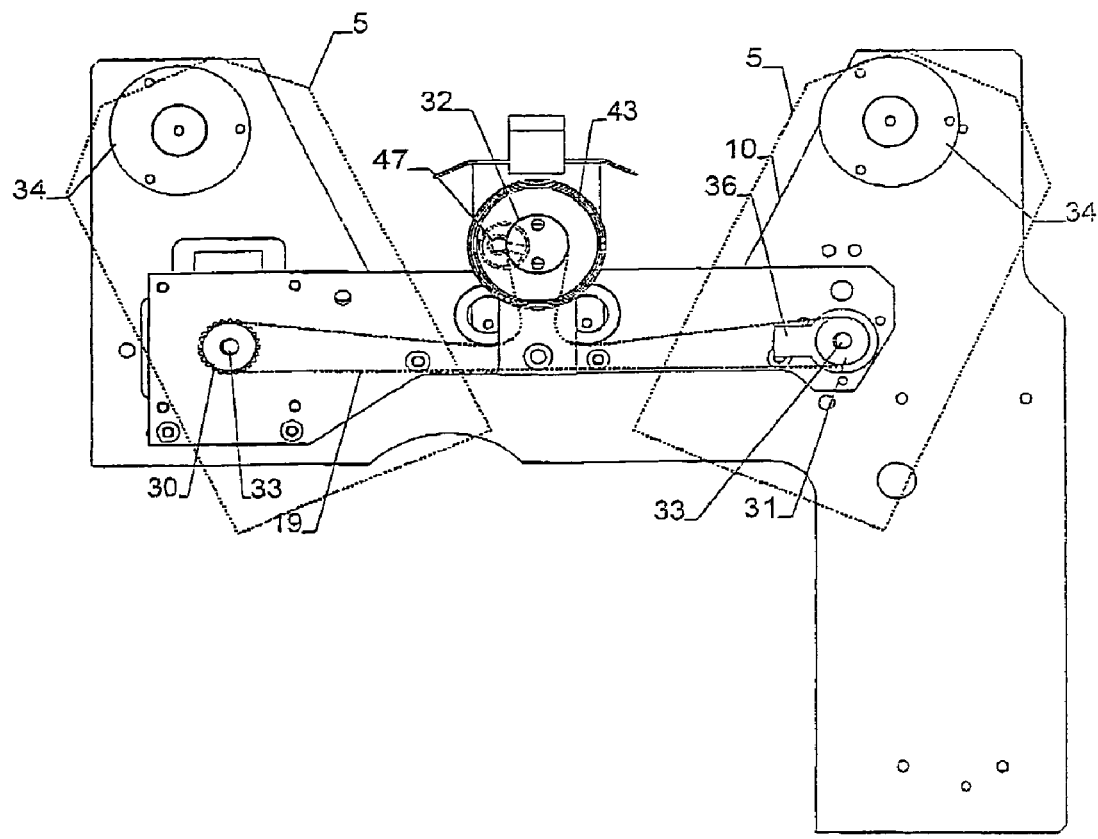
FIG. 7 is a top view of the base plate of the embodiment of FIG. 4 with the belt pulleys, wherein the course of the belt and the arrangement of the storage racks are shown in dashed lines.

As can be seen from FIG. 7, an arm 36 is mounted to one gear, the position of which can be detected by a sensor. This allows to determine the absolute position of rack carrier 8, such that it can be brought into a defined position (e.g. for being accessed by an automated robot system).

To keep the lateral oscillations of the storage racks small, in particular in the upper end sections thereof, the embodiment of FIGS. 4-7 comprises a counterweight assembly 40 between the two storage racks 5. It comprises a moving part, which is located between a lower support 41 and an upper support 42. Lower support 41 is located at the height of rack carrier 8 and extends, in order to achieve a stable and compact design, through an opening or recess 48 of the same. It is mounted to base body 10. Upper support 42 is located at the height of upper end section 50 of the storage racks and is mounted to a strut 49, which in its turn is rigidly but releasably connected to the top end of both storage racks 5.

Figure 8:
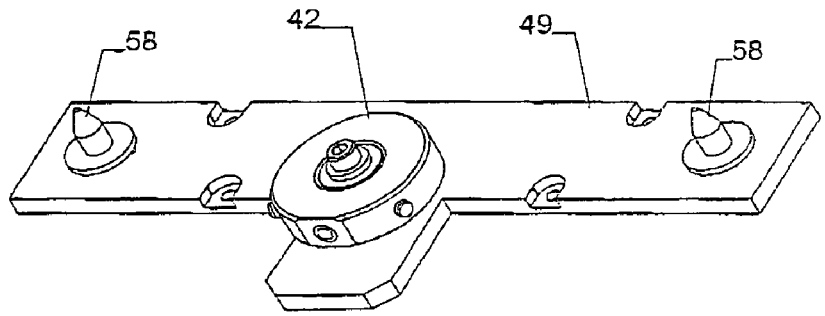
FIG. 8 shows the upper strut of the counterweight assembly.

FIG. 8 shows strut 49 from below. Two pins 58 can be seen, which releasably engage the storage racks 5 as well as upper support 42.

Each support 41, 42 has a rotating table 43, 44, which is rotatable about a vertical counterweight axis 45. Lower rotating table 43 is driven by means of gear 32 and gear belt 19, namely with the same rotational speed as and in synchronicity with the gears 30, 31. Upper rotating table 44 is not actively driven but can rotate freely about counterweight axis 45.

A rod-shaped counterweight carrier 47 extends vertically between the two rotating tables 43, 44, approximately from the height of rack carrier 8 to the height of upper end section 50 of the storage racks 5. It is arranged eccentrically in respect to counterweight axis 45. A counterweight 52 is mounted to counterweight carrier 47, namely at a height between rack carrier 8 and upper end section 50. Advantageously, counterweight 52 can be displaced along counterweight carrier 47 and can be locked in position at the desired height.

As mentioned, the gears 30, 31 and 32 are driven synchronously by means of gear belt 19 and have the same speed of rotation (i.e. rate of rotation). Hence, a fixed phase relation exists between the position of the eccentric pins 33 and the one of lower rotating table 43. This phase relation is advantageously chosen such that there is no mutual phase difference between the positions of the pins, but that there is a 180° phase difference between the positions of the pins and the one of lower rotating table 43 (i.e. of counterweight carrier 47 mounted thereto). When motor 20 is set into motion, counterweight carrier 47 is moving oppositely to rack carrier 8, such that it counteracts the oscillations caused by shaking to storage racks.

It is advantageous if the mass of the moving part of counterweight assembly 40 multiplied with the amplitude of motion of the moving part is substantially equal to the sum of the masses of all storage racks 5 and the rack carrier 8 multiplied with the amplitude of motion of rack carrier 8. As can in particular be seen in FIG. 7, the shown embodiment uses a much larger amplitude of motion of the moving part of counterweight assembly 40 than the amplitude of motion of the pins 33 and therefore of rack carrier 8, for which reason the mass of the moving part of counterweight assembly 40 can be comparatively small.

Figure 6:
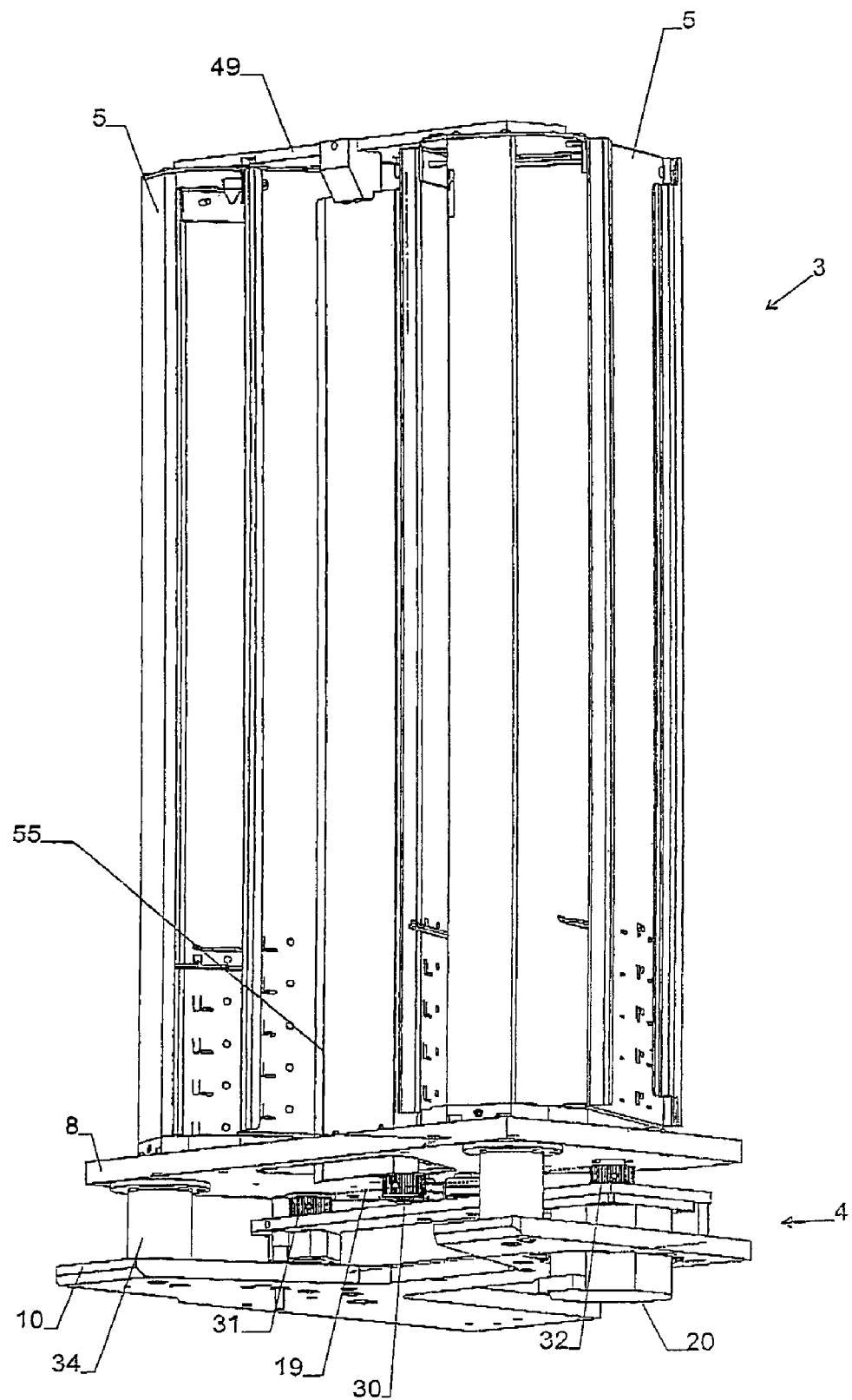
FIG. 6 is the embodiment of FIG. 4 seen from a further angle, with an additional protecting plate.

Counterweight assembly 40 can be covered by a protective plate 55, as it is e.g. shown in FIG. 6.

To save space, counterweight assembly 40 of the shown embodiment is arranged between the two storage racks 5. In a star-shaped or carousel-shaped arrangement of the type of FIG. 3, counterweight assembly 40 can be located in the center of the carousel.

Figure 9:
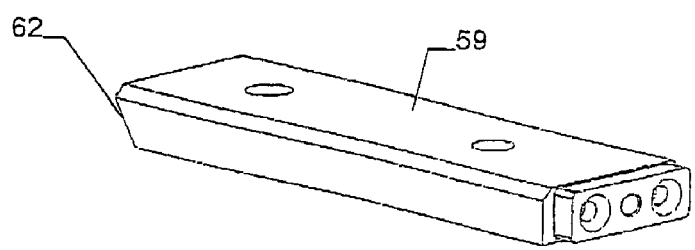
FIG. 9 shows a holder rail for a storage rack.

In view of the shaking motion of all the embodiments shown here, the storage racks 5 should be well affixed to rack carrier 8. For this purpose, a holder rail 59 is arranged for each storage rack 5 on rack carrier 8, as shown in FIG. 4 and in particular in FIG. 9. Each holder rail 59 is received in a recess 60 at the foot of each storage rack 5 and is held in centered manner by means of horizontal grub screws 61 (see FIG. 4), by means of which the storage racks 5 can be clamped to the guide rails 59. The holder rails 59—as well as the corresponding recesses 60 at the feet of the storage racks 5—comprise an inclined face 62 at a site opposite to the grub screws 61 (see FIG. 9) for centering and fixing the storage racks 5 on rack carrier 8.

Figure 10:
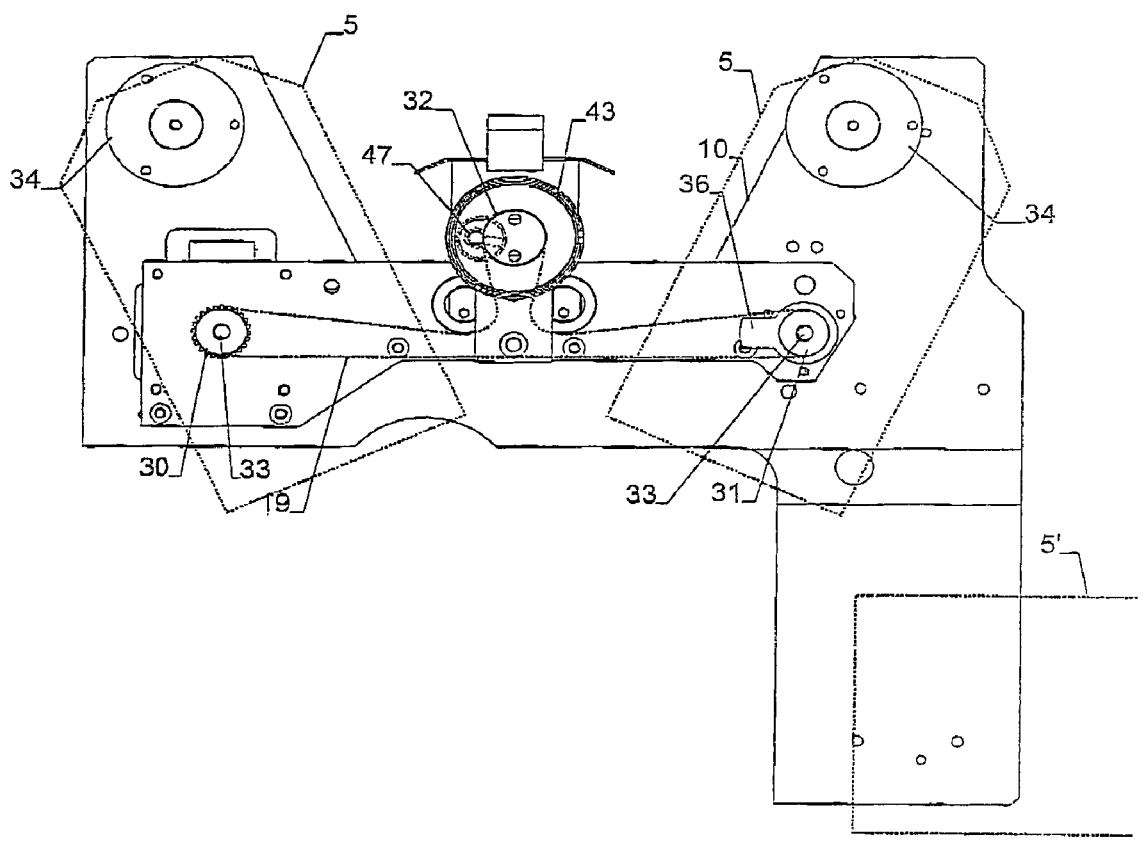
FIG. 10 shows a variant of the embodiment of FIG. 7.

In the embodiments shown so far all storage racks are shaken. It is, however, also possible to shake only one set of the storage racks while leaving another set at rest, even when the shaker drive is activated. A corresponding arrangement is illustrated in FIG. 10. It shows a device which is basically built in the same manner as the one of FIG. 7, but which comprises a third additional storage rack 5'. The latter does not rest on the (shaking) rack carrier 8, but on the stationary base body 10. Hence, the third storage rack 5' remains stationary even when shaker drive 4 is active.

It is also possible to provide two rack carriers which can be shaken selectively, either by means of two separate shaker drives of by means of an selectable transmission between the two rack carriers to a common shaker drive.

While there are shown and described presently preferred embodiments of the invention, it is to be distinctly understood that the invention is not limited thereto but may be otherwise variously embodied and practised within the scope of the following claims.

The invention claimed is:
1. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other, a counterweight assembly connected to an upper end section of the storage rack and being driven to exert a force opposite to the shaking motion in order to counteract an oscillation of the upper end section of the storage rack, and a moving part driven to move opposite to the shaking motion, wherein the moving part comprises a vertically displaceable counterweight.

2. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other,
a counterweight assembly connected to an upper end section of the storage rack and being driven to exert a force opposite to the shaking motion in order to counteract an oscillation of the upper end section of the storage rack, and
a moving part driven to move opposite to the shaking motion, wherein said moving part is moveable between an upper and an lower support, wherein the upper support is rigidly connected to the upper end section of the of the storage rack.

3. The storage device of claim 2 further comprising rotating tables mounted to the upper and lower supports for eccentrically mounting said moving part.

4. The storage device of claim 3 further comprising an eccentric member, wherein said rack carrier is mounted to said eccentric member and wherein the rotating table and the eccentric member are driven synchronously and with equal rotational speed.

5. The storage device of claim 4 further comprising a driving belt for commonly driving said eccentric member and said rotating table.

6. The storage device of claim 2 wherein the upper support comprises a strut connected to the upper end section of the storage rack.

7. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other,
a counterweight assembly connected to an upper end section of the storage rack and being driven to exert a force opposite to the shaking motion in order to counteract an oscillation of the upper end section of the storage rack, and
a moving part driven to move opposite to the shaking motion, wherein a mass of the moving part multiplied by an amplitude of motion of the moving part corresponds substantially to a mass of the storage rack or storage racks and the rack carrier multiplied by an amplitude of motion of the rack carrier.

8. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other,
a counterweight assembly connected to an upper end section of the storage rack and being driven to exert a force opposite to the shaking motion in order to counteract an oscillation of the upper end section of the storage rack, and a moving part driven to move opposite to the shaking motion, wherein an amplitude of motion of the moving part is larger than an amplitude of motion of the rack carrier.

9. A storage device for laboratory samples comprising:
a shaker drive,
a rack carrier being driven by said shaker drive for performing a shaking motion with horizontal component,
at least two storage racks arranged on the rack carrier, which storage racks comprise storage locations for a plurality of laboratory samples on top of each other,
a counterweight assembly connected to an upper end section of the storage rack and being driven to exert a force opposite to the shaking motion in order to counteract an oscillation of the upper end section of the storage rack, and
an upper support comprising a strut connected to the upper end sections of all storage racks.

10. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other, and
a counterweight assembly connected to an upper end section of the storage rack and being driven to exert a force opposite to the shaking motion in order to counteract an oscillation of the upper end section of the storage rack, wherein the counterweight assembly extends through an opening or recess of the rack carrier.

11. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other, and
a counterweight assembly connected to an upper end section of the storage rack and being driven to exert a force opposite to the shaking motion in order to counteract an oscillation of the upper end section of the storage rack, wherein the counterweight assembly comprises a counterweight carrier extending from a height of said rack carrier to a height of the upper end section.

12. The storage device of claim 11, wherein the counterweight carrier is driven to an oscillating motion in opposite phase to the shaking motion.

13. The storage device of claim 12 further comprising a counterweight mounted on the counterweight carrier arranged between the height of the rack carrier and the height of the upper end section.

14. A storage device for laboratory samples comprising:
a shaker drive,
a rack carrier being driven by said shaker drive for performing a shaking motion with horizontal component,
at least one storage rack arranged on the rack carrier, which storage rack comprises storage locations for a plurality of laboratory samples on top of each other, and
a counterweight assembly connected to an upper end section of the storage rack and being driven to exert a force opposite to the shaking motion in order to counteract an oscillation of the upper end section of the storage rack, comprising several storage racks and operable to shake only a first set of said storage racks while a second set of said storage racks remains at rest.

15. A storage device for laboratory samples comprising:
a shaker drive,
a rack carrier being driven by said shaker drive for performing a shaking motion with horizontal component,
at least one storage rack arranged on the rack carrier, which storage rack comprises vertical side walls having a plurality of ledges forming storage locations for a plurality of laboratory samples on top of each other,
a counterweight assembly connected to an upper end section of the storage rack and being driven to exert a force opposite to the shaking motion in order to counteract an oscillation of the upper end section of the storage rack,
a carousel carrying a plurality of said storage racks, and
a rotational drive for rotating the carousel about a vertical axis.

16. The storage device of claim 15 wherein the counterweight assembly comprises a moving part driven to move opposite to the shaking motion.

17. The storage device of claim 15 comprising at least two storage racks, wherein the counterweight assembly is arranged between the storage racks.

18. The storage device of claim 15 wherein the storage racks are adapted to receive micro titer plates.

19. A climate controlled cabinet comprising the storage device of claim 15.

* * * * *